United States Patent
Johnson et al.

(10) Patent No.: US 7,846,488 B2
(45) Date of Patent: Dec. 7, 2010

(54) MASKING METHOD FOR COATING A MICRONEEDLE ARRAY

(75) Inventors: Peter R. Johnson, Eagan, MN (US);
Marla R. Emery, Woodbury, MN (US);
James T. Wolter, Oakdale, MN (US);
Jennifer E. Raeder-Devens, Highland Park, IL (US); Daniel C. Duan, St. Paul, MN (US); Moses M. David, Woodbury, MN (US); Hye-Ok Choi, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 872 days.

(21) Appl. No.: 11/718,737

(22) PCT Filed: Nov. 18, 2005

(86) PCT No.: PCT/US2005/041858
§ 371 (c)(1),
(2), (4) Date: May 7, 2007

(87) PCT Pub. No.: WO2006/055799
PCT Pub. Date: May 26, 2006

(65) Prior Publication Data
US 2008/0102192 A1     May 1, 2008

Related U.S. Application Data

(60) Provisional application No. 60/629,209, filed on Nov. 18, 2004.

(51) Int. Cl.
*A61L 33/00* (2006.01)
(52) U.S. Cl. .......... 427/2.1; 604/191; 604/239; 604/272; 324/754; 427/299
(58) Field of Classification Search .......... 427/2.1
See application file for complete search history.

(56) References Cited

U.S. PATENT DOCUMENTS

| | | |
|---|---|---|
| 2,619,962 A | 12/1952 | Rosenthal |
| 3,072,122 A | 1/1963 | Rosenthal |
| 3,136,314 A | 6/1964 | Kravitz |

(Continued)

FOREIGN PATENT DOCUMENTS

WO   WO 96/10630   4/1996

(Continued)

OTHER PUBLICATIONS

U.S. Appl. No. 60/578,651, filed Jun. 10, 2004, Frederickson et al.

(Continued)

*Primary Examiner*—Michael Barr
*Assistant Examiner*—Andrew Bowman (57) ABSTRACT

A method of coating a microneedle array comprising: providing a microneedle array having a substrate and at least one needle; providing a removable masking layer on the microneedle array such that the substrate is at least partially covered by the masking layer and the at least one needle remains at least partially exposed; and applying a coating material to at least a portion of the exposed portion of the microneedle array.

28 Claims, 5 Drawing Sheets

U.S. PATENT DOCUMENTS

| | | | |
|---|---|---|---|
| RE25,637 E | 9/1964 | Kravitz et al. |
| 3,221,740 A | 12/1965 | Rosenthal |
| 3,466,131 A | 9/1969 | Arcudi |
| 3,675,766 A | 7/1972 | Rosenthal |
| 3,678,150 A | 7/1972 | Szumski et al. |
| 3,688,764 A | 9/1972 | Reed et al. |
| 3,964,482 A | 6/1976 | Gerstel et al. |
| 4,473,083 A | 9/1984 | Maganias |
| 4,474,751 A | 10/1984 | Haslam et al. |
| 4,921,475 A | 5/1990 | Sibalis |
| 5,192,535 A | 3/1993 | Davis et al. |
| 5,250,023 A | 10/1993 | Lee et al. |
| 5,279,544 A | 1/1994 | Gross et al. |
| 5,340,572 A | 8/1994 | Patel et al. |
| 5,402,798 A | 4/1995 | Swierczek et al. |
| 5,440,446 A | 8/1995 | Shaw et al. |
| 5,611,806 A | 3/1997 | Jang |
| 5,879,326 A | 3/1999 | Godshall et al. |
| 5,983,136 A | 11/1999 | Kamen |
| 6,050,988 A | 4/2000 | Zuck et al. |
| 6,091,975 A | 7/2000 | Daddona et al. |
| 6,132,755 A | 10/2000 | Eicher et al. |
| 6,219,574 B1 | 4/2001 | Cormier et al. |
| 6,256,533 B1 | 7/2001 | Yuzhakov et al. |
| 6,312,612 B1 | 11/2001 | Sherman et al. |
| 6,322,808 B1 | 11/2001 | Trautman et al. |
| 6,334,856 B1 * | 1/2002 | Allen et al. ................. 604/191 |
| 6,440,096 B1 | 8/2002 | Lastovich et al. |
| 6,454,755 B1 | 9/2002 | Godshall |
| 6,503,231 B1 | 1/2003 | Prausnitz et al. |
| 6,532,386 B2 | 3/2003 | Sun et al. |
| 6,537,242 B1 | 3/2003 | Palmer |
| 6,547,755 B1 | 4/2003 | Lippe et al. |
| 6,589,202 B1 | 7/2003 | Powell |
| 6,591,124 B2 | 7/2003 | Sherman et al. |
| 6,595,947 B1 | 7/2003 | Mikszta et al. |
| 6,603,998 B1 | 8/2003 | King et al. |
| 6,611,707 B1 | 8/2003 | Prausnitz et al. |
| 6,623,457 B1 | 9/2003 | Rosenberg |
| 6,656,147 B1 | 12/2003 | Gertsek et al. |
| 6,689,100 B2 | 2/2004 | Connelly et al. |
| 6,713,291 B2 | 3/2004 | King et al. |
| 6,743,211 B1 | 6/2004 | Prausnitz et al. |
| 6,797,276 B1 | 9/2004 | Glenn et al. |
| 6,855,131 B2 | 2/2005 | Trautman et al. |
| 6,881,203 B2 | 4/2005 | Delmore et al. |
| 6,881,538 B1 | 4/2005 | Haddad et al. |
| 6,908,453 B2 | 6/2005 | Fleming et al. |
| 6,931,277 B1 | 8/2005 | Yuzhakov et al. |
| 2001/0044606 A1 | 11/2001 | Inkpen et al. |
| 2002/0082543 A1 | 6/2002 | Park et al. |
| 2002/0091357 A1 | 7/2002 | Trautman et al. |
| 2002/0095134 A1 | 7/2002 | Pettis et al. |
| 2002/0102292 A1 | 8/2002 | Cormier et al. |
| 2002/0128599 A1 | 9/2002 | Cormier et al. |
| 2002/0132054 A1 | 9/2002 | Trautman et al. |
| 2002/0138049 A1 | 9/2002 | Allen et al. |
| 2002/0169416 A1 | 11/2002 | Gonnelli et al. |
| 2002/0177839 A1 | 11/2002 | Cormier et al. |
| 2002/0177858 A1 | 11/2002 | Sherman et al. |
| 2002/0193729 A1 | 12/2002 | Cormier et al. |
| 2002/0198509 A1 | 12/2002 | Mikszta et al. |
| 2003/0036710 A1 | 2/2003 | Matriano et al. |
| 2003/0045837 A1 | 3/2003 | Delmore et al. |
| 2003/0083641 A1 | 5/2003 | Angel et al. |
| 2003/0135161 A1 | 7/2003 | Fleming et al. |
| 2003/0187394 A1 | 10/2003 | Wilkinson et al. |
| 2003/0187395 A1 | 10/2003 | Gabel et al. |
| 2003/0199812 A1 | 10/2003 | Rosenberg |
| 2003/0208167 A1 | 11/2003 | Prausnitz et al. |
| 2004/0039343 A1 | 2/2004 | Eppstein et al. |
| 2004/0049150 A1 | 3/2004 | Dalton et al. |
| 2004/0077994 A1 | 4/2004 | Lastovich et al. |
| 2004/0106904 A1 | 6/2004 | Gonnelli et al. |
| 2004/0138612 A1 | 7/2004 | Shermer et al. |
| 2004/0176732 A1 | 9/2004 | Frazier et al. |
| 2005/0025778 A1 | 2/2005 | Cormier et al. |
| 2005/0027242 A1 | 2/2005 | Gabel et al. |
| 2005/0049549 A1 | 3/2005 | Wong et al. |
| 2005/0065463 A1 | 3/2005 | Tobinaga et al. |
| 2005/0065466 A1 | 3/2005 | Vedrine |
| 2005/0065472 A1 | 3/2005 | Cindrich et al. |
| 2005/0089554 A1 | 4/2005 | Cormier et al. |
| 2005/0106226 A1 | 5/2005 | Cormier et al. |
| 2005/0106227 A1 | 5/2005 | Zalipsky et al. |
| 2005/0261631 A1 | 11/2005 | Clarke et al. |

FOREIGN PATENT DOCUMENTS

| | | |
|---|---|---|
| WO | WO 00/74766 | 12/2000 |
| WO | WO 01/36037 | 5/2001 |
| WO | WO 02/30281 | 4/2002 |
| WO | WO 02/085447 | 10/2002 |
| WO | WO 03/092785 | 11/2003 |
| WO | WO 2005/051455 | 6/2005 |
| WO | WO 2005/051476 | 6/2005 |
| WO | WO 2005/058393 | 6/2005 |
| WO | WO 2005/065765 | 7/2005 |
| WO | WO 2005/082596 | 9/2005 |

OTHER PUBLICATIONS

Daddona Current Opinion in Drug Discovery and Development 1999 2(2);168-171.

Kaushik et al. Current Opinion in Drug Discovery and Development 1999 2(2);168-171.

Henry et al. J. Pharm.Sci., 1998, 87,8,922-925.

McAllister et al. (1) Annual Review of Biomedical Engineering, 2000, 2, 289-313.

McAllister et al. (2) Proceed. Int'l. Symp. Control Release of Bioactive Material, 26, (1999), CRS, 192-193.

* cited by examiner

MASKING METHOD FOR COATING A MICRONEEDLE ARRAY

CROSS REFERENCE TO RELATED APPLICATIONS

This application is a national stage filing under 35 U.S.C. 371 of PCT/US2005/041858 filed Nov. 18, 2005, which claims priority to 60/629,209; filed Nov. 18, 2004 the disclosure of which is incorporated by reference in its/their entirety herein.

FIELD

The present invention relates to methods of coating a microneedle array.

BACKGROUND

Only a limited number of molecules with demonstrated therapeutic value can be transported through the skin, even with the use of approved chemical enhancers. The main barrier to transport of molecules through the skin is the stratum corneum the outermost layer of the skin).

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can pass through that layer and into the tissues below.

Microneedle devices having a fluid reservoir and conduits through which a therapeutic substance may be delivered to the skin have been proposed, but there remain a number of difficulties with such systems, such as the ability to make very fine channels that can reliably be used for fluid flow.

Microneedle devices having a dried coating on the surface of a microneedle array have desirable features compared to fluid reservoir devices. The devices are generally simpler and can directly inject a therapeutic substance into the skin without the need for providing reliable control of fluid flow through very fine channels in the microneedle device.

SUMMARY OF THE INVENTION

The ability to provide a consistent coating in one or more desired locations on the microneedle array is an important feature for a microneedle device having a dried coating. Although there are numerous well known methods for providing dried coatings on generally flat surfaces, coating of a microneedle array provides a challenge due to the high surface irregularity inherent in any array design.

It has now been found that the rate of drying and the location of coating of a coating fluid may be adjusted and controlled by masking the substrate of a microneedle array.

The present invention provides, among other things, a method of coating a microneedle array comprising providing a microneedle array having a substrate and at least one needle, providing a removable masking layer on the microneedle array such that the substrate is at least partially covered by the masking layer and the at least one needle remains at least partially exposed, and applying a coating material to at least a portion of the exposed portion of the microneedle array.

The invention will be further understood by those skilled in the art upon consideration of the remainder of the disclosure, including the Detailed Description and the appended claims.

As used herein, certain terms will be understood to have the meaning set forth below:

"Array" refers to the medical devices described herein that include one or more structures capable of piercing the stratum corneum to facilitate the transdermal delivery of therapeutic agents or the sampling of fluids through or to the skin.

"Microstructure," "microneedle" or "microarray" refers to the specific microscopic structures associated with the array that are capable of piercing the stratum corneum to facilitate the transdermal delivery of therapeutic agents or the sampling of fluids through the skin. By way of example, microstructures can include needle or needle-like structures as well as other structures capable of piercing the stratum corneum.

The features and advantages of the present invention will be understood upon consideration of the detailed description of the preferred embodiment as well as the appended claims. These and other features and advantages of the invention may be described below in connection with various illustrative embodiments of the invention. The above summary of the present invention is not intended to describe each disclosed embodiment or every implementation of the present invention. The Figures and the detailed description which follow more particularly exemplify illustrative embodiments.

BRIEF DESCRIPTION OF THE DRAWINGS

Preferred embodiments of the invention will now be described in greater detail below with reference to the attached drawings, wherein.

DETAILED DESCRIPTION

Figure 1:
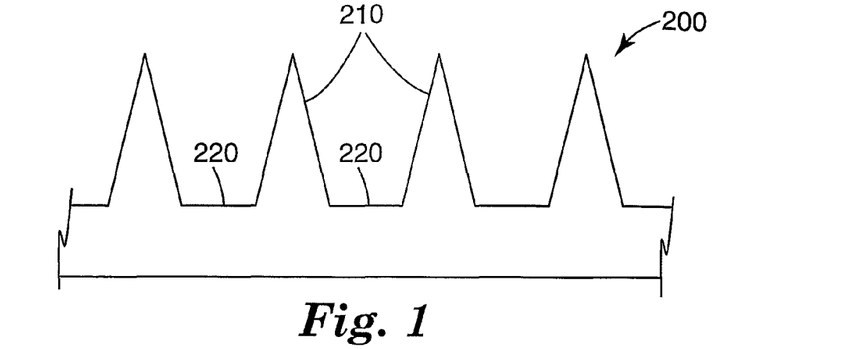
FIG. 1 is a schematic cross-sectional view of an uncoated microneedle array.
Figure 2:
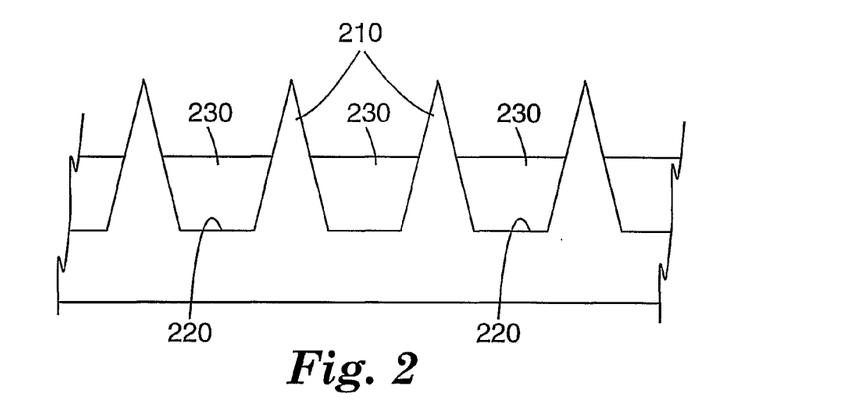
FIG. 2 is a schematic cross-sectional view of the array with a masking fluid having been applied to the substrate.

One embodiment of the method of the present invention is shown in FIGS. 1 to 3. FIG. 1 shows an uncoated microneedle array 200 having a substrate 220 and microneedles 210 protruding from the substrate 220. A masking fluid 230 is applied to the microneedle array 200 (as shown in FIG. 2) thereby coating the substrate 220. A coating fluid 235 is then applied (as shown in FIG. 3A). The coating fluid 235 is desirably applied such that it does not disturb the masking fluid 230.

Figure 3A:
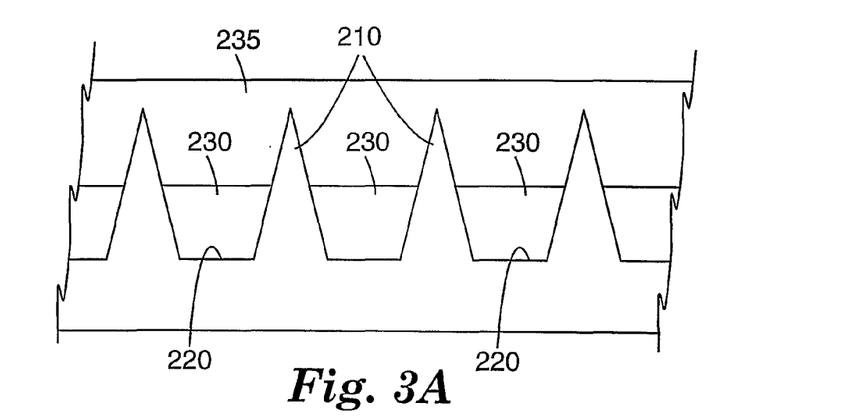
FIG. 3A is a schematic cross-sectional view of the array with a coating fluid having been applied.
Figure 3B:
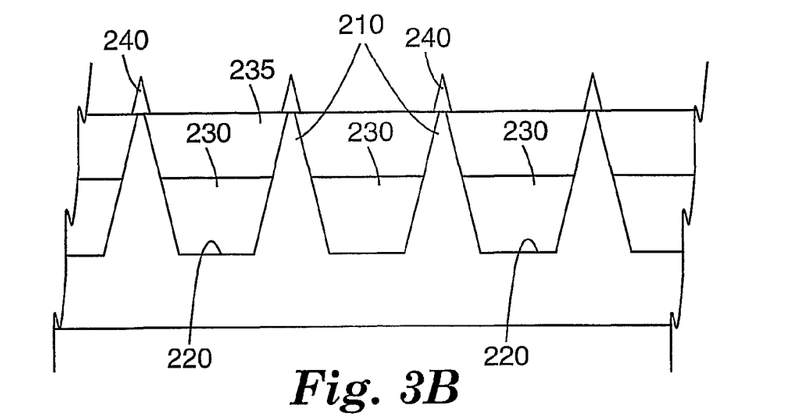
FIG. 3B is a schematic cross-sectional view of the array as part of the coating fluid has evaporated.
Figure 3C:
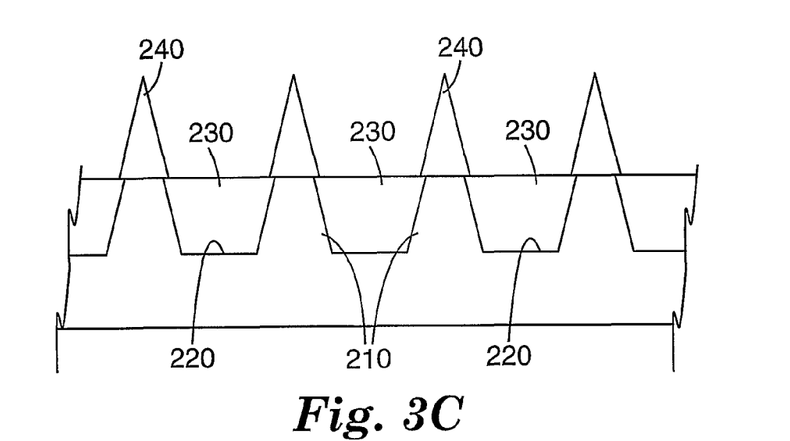
FIG. 3C is a schematic cross-sectional view of the array as the coating fluid has evaporated to leave a dried coating.
Figure 3D:
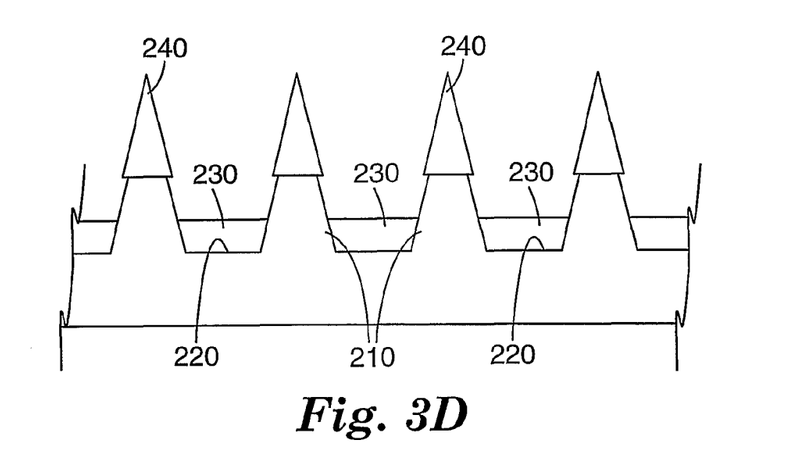
FIG. 3D is a schematic cross-sectional view of the array as part of the masking fluid has evaporated.
Figure 3E:
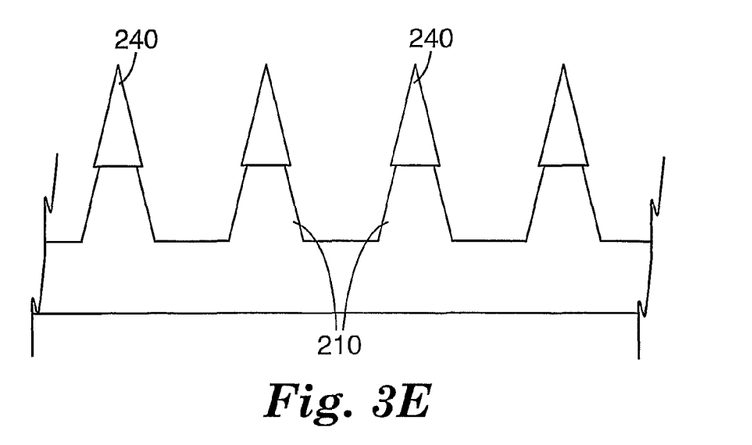
FIG. 3E is a schematic cross-sectional view of the array as the masking fluid has evaporated leaving an array with a dried coating on the needle tips.

The coating fluid 235 desirably forms a separate layer above the masking fluid 230. As shown in FIG. 3B, the coating fluid has partially evaporated. As shown in FIG. 3C, the coating fluid has completely evaporated to leave a dried coating 240 on the tips of the microneedles 210. As shown in FIG. 3D, the masking fluid 230 has partially evaporated. As shown in FIG. 3E, the masking fluid 230 has completely evaporated.

It should be understood that the sequence of evaporation described above need not occur in such a discrete, step-wise fashion. That is, the coating fluid and masking fluid may both be evaporating at the same time, such that the level of masking fluid may be dropping as shown in FIG. 3B before all of the coating fluid has evaporated. Likewise, the dried coating shown in FIG. 3E may take on any of a number of different shapes. As shown, it may be a thin laminar coating on the upper portion of each microneedle, but it may also form more of a droplet shape on the tip or partially coat the lower portions of the microneedle as well. It may be desirable to adjust the relative rates of evaporation and/or mixing of the masking and coating fluids in order to adjust the location of the dried coating. Portions of the dried coating may also be deposited on the substrate.

Figure 4:
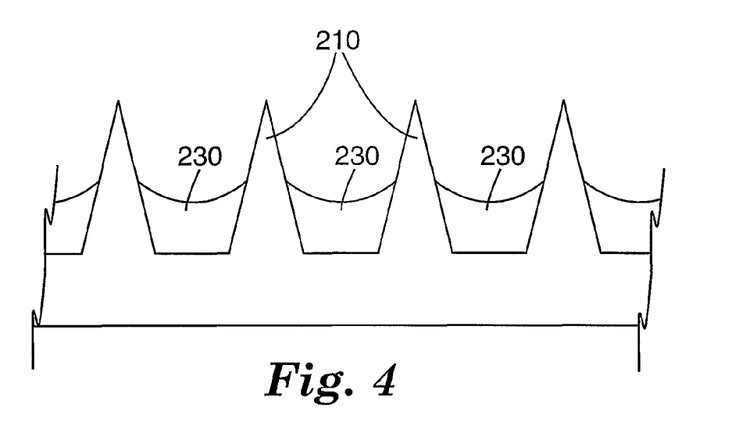
FIG. 4 is a schematic cross-sectional view of another embodiment of a microneedle array with a masking fluid applied to the substrate.

The masking fluid need not uniformly cover the substrate as shown in FIG. 2, but may form a meniscus due to surface tension effects, such as is shown in FIG. 4. This meniscus is shown as a concave shape, but it may also be a convex shape. The shape of the meniscus may be adjusted by a number of factors, including the type of masking fluid, the type of material of the substrate and microneedles, the size of the microneedles, the spacing between the microneedles, and any surface treatments of the substrate and/or microneedles.

In one embodiment (not shown), the masking fluid may initially be applied so that it covers all of the microneedles. The masking fluid may then be allowed to partially evaporate or otherwise be partially removed so as to partially expose the microneedles to which a coating material is applied. The coating material may be subsequently applied after the microneedles are exposed or the coating material may be applied on top of the masking fluid while the masking fluid still fully covers the microneedles. As the masking fluid is removed to expose the array, then the coating material is subsequently applied to the exposed portion of the microneedle array.

The type of masking fluid selected may vary widely and may depend on a number of factors, including the type of material of the substrate and microneedles, the size of the microneedles, the spacing between the microneedles, any surface treatments of the substrate and/or microneedles, the type of coating fluid, any therapeutic agents contained within the coating fluid, and the application for which the dry-coated microneedle array is intended.

In one aspect, the density of the masking layer fluid is higher than the density of the coating solution. The microneedle array will typically be placed in an orientation where the substrate is supported from below and the coating fluid is applied from above. In this case the higher density of the masking layer fluid may help to prevent or minimize mixing of the masking fluid and coating solution. In one aspect, the masking fluid is substantially immiscible with the coating fluid. By substantially immiscible it should be understood that the masking fluid and coating fluid need not be completely immiscible, but that the relative solubility of one in the other is relatively small and insignificant, for example, the solubility of masking fluid in the coating fluid (or vice-versa) would be less than about 5% by weight, preferably less than about 1% by weight. In one aspect, one or more solutes contained within the coating fluid are substantially insoluble within the masking fluid. By substantially insoluble it should be understood that the one or more solutes need not be completely insoluble, but that the solubility of the one or more solutes is relatively small and insignificant, for example, the solubility of a coating fluid solute in the masking fluid would be less than 10%, and preferably less than 1%, of the solubility of the solute in the coating fluid.

In one aspect, the masking fluid desirably has a vapor pressure lower than that of the coating fluid. That is, the volatility of the masking layer fluid is lower than that of the coating fluid. This may aid in allowing the coating fluid to substantially evaporate before the masking fluid evaporates. In one embodiment, volatility or vapor pressure may be determined and compared at a drying temperature to which both the masking fluid and coating fluid are subjected. Drying of the masking and/or coating fluids may be done at any suitable temperature. For example, drying may be performed at ambient conditions (e.g., approximately 20 to 23° C.) with essentially no restriction to evaporation other than that naturally provided by typical atmospheric conditions. Alternatively, the rate of drying may be altered by holding the array in an environment that is partially or fully saturated with the masking and/or coating fluid vapor. This may be done by directly adding vapor to the environment surrounding the array or by placing the array in a partially closed environment so as to allow a build-up of vapor in the area surrounding the array. For example, an array may be held in a closed petri dish during drying. In still another alternative, the array may be held in a drying oven which can combine increased temperature and/or air flow to accelerate the rate of drying. In still another alternative, the masking fluid may be held at a differential temperature from the coating fluid (e.g., a lower temperature) in order to facilitate differential evaporation of the two fluids. In one alternative, it may be desirable to adjust the vapor pressure of the masking fluid such that it evaporates at about the same rate as the coating fluid or at a rate faster than that of the coating fluid. Such an adjustment may allow, for instance, coating of the entire sides of the microneedles or a partial coating of the substrate, which may be desirable depending on the intended use of the dry-coated microneedle array. In another embodiment, the masking fluid may be simply poured off of the substrate after allowing the coating solution to dry.

Fluorinated solvents, such as hydrofluoroethers, hydrofluoroalkanes, perfluoroalkanes, and other perfluorinated compounds may be particularly suitable for use as the masking fluid as they have a relatively high density and are relatively immiscible with water and/or many conventional organic solvents. Examples of suitable fluorinated solvents include 3-ethoxy-1,1,1,2,3,4,4,5,5,6,6,6-dodecafluoro-2-trifluoromethyl-hexane (available as 3M™ Novec™ Engineered Fluid HFE-7500 from 3M Co.), ethyl nonafluoroisobutyl ether and ethyl nonafluorobutyl ether (a mixture of which is available as 3M™ Novec™ Engineered Fluid HFE-7200 from 3M Co.), FC-43 FLUORINERT™ Electronic Liquid (a mixture of primarily 12 carbon perfluoro compounds available from 3M Co.), and FC-5312 FLUORINERT™ Electronic Liquid (a mixture of primarily 15 carbon perfluoro compounds available from 3M Co.). Water may be suitable as a masking fluid, for example, when the coating solution comprises a lower density organic solvent such as hexane or heptane The coating solution comprises a carrier fluid or solvent and at least one dissolved or dispersed material that will ultimately become the dried coating on the microneedle array. The carrier fluid or solvent should be selected such that it may dissolve or disperse the material intended for coating. Dispersed material may be in the form of a suspension, that is, as particles dispersed or suspended in a carrier fluid or solvent. Examples of suitable carrier fluids or solvents include water, ethanol, methanol, isopropanol, ethyl acetate, hexane, and heptane. The coating solution may contain additional excipients such as viscosity modifiers, stabilizers, surfactants, and other additives. Examples of suitable additional excipients include sucrose, trehalose, raffinose, lactose, ovalbumin, potassium citrate, polyvinyl pyrrolidone, polyoxyethylene sorbitan esters (i.e., polysorbates), and hydroxyethyl cellulose. In one embodiment, the coating solution will preferably wet the masking layer, that is, it will spread relatively uniformly across the masking layer. Such spreading will desirably lead to a relatively uniform application of coated material to the microneedle array. Alternatively, the surface properties of the coating solution and/or masking fluid may be adjusted to control the amount of spreading of the coating solution, thereby allowing for application of controlled amounts of coating material at specified locations on the microneedle array. Evaporation of the carrier fluid may be allowed to take place at ambient conditions or may be adjusted by altering the temperature or pressure of the atmosphere surrounding the microneedle array. Evaporation conditions are desirably selected so as to avoid degradation of the coating material.

A second masking fluid may be optionally added after addition of the first masking fluid to the microneedle array. For example, a hydrofluoroether masking fluid may be added to the array followed by addition of ethanol to prepare the masking layer. The coating solution is then subsequently added as described above. The second masking fluid may aid in altering relative rates of evaporation or adjusting surface tensions between differing fluids.

Figure 5:
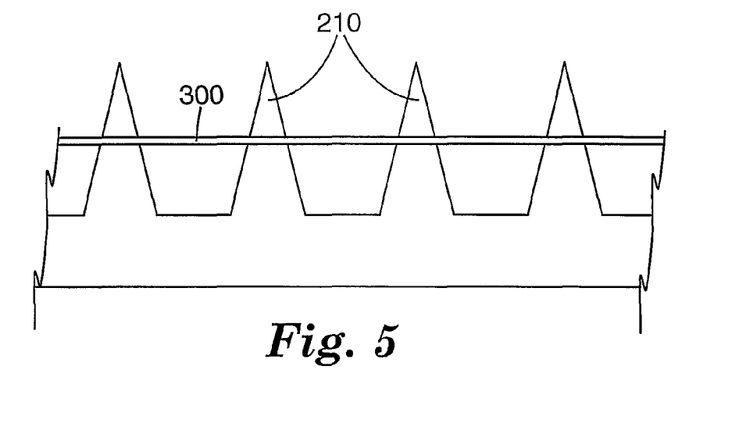
FIG. 5 is a schematic cross-sectional view of a microneedle array with a masking film applied.
Figure 6A:
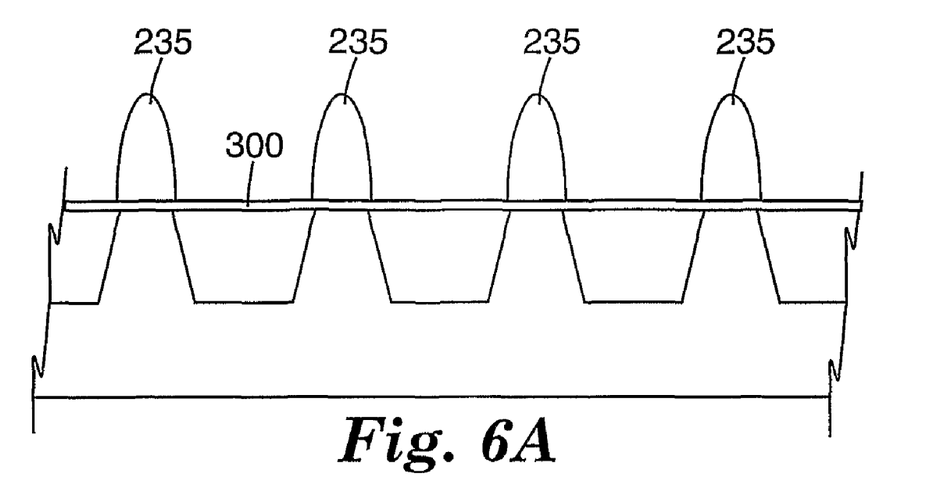
FIGS. 6A, B are a schematic cross-sectional view and a plan view of the microneedle array of FIG. 5 with a coating fluid having been applied.
Figure 6B:
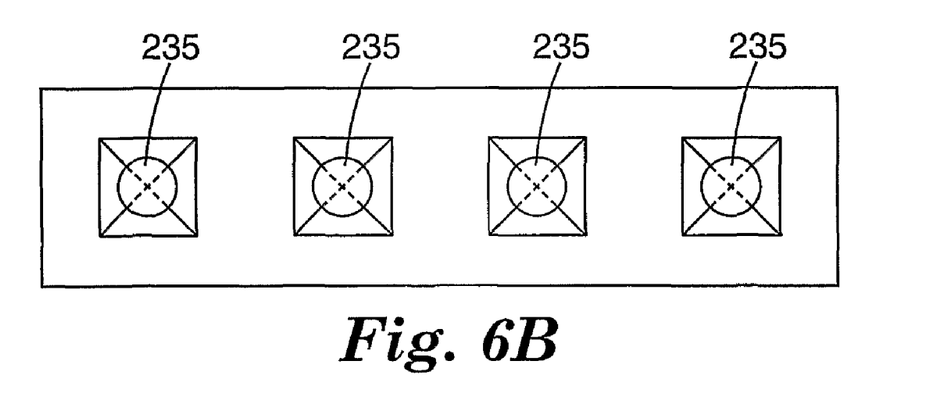

In another embodiment, the coating may be applied directly as a solid, such as by spray coating, in which case a carrier fluid is optional or unnecessary. In another embodiment, the masking layer may be in the form of a solid or semi-solid layer. A masking layer in the form of a masking film 300 is shown in FIG. 5. Such a film may be, for example, a thin polymeric film that is pierced by the microneedles to a predetermined height so that only the microneedle tips are exposed. As shown in FIG. 6, a coating solution may be applied to the needle tips. The coating solution may also be applied as a continuous layer, such as that shown in FIG. 3A.

Dried coating material is deposited on the microneedle array. In one embodiment, the dried coating material is preferentially deposited on the microneedles. By preferentially deposited it is meant that the amount of dried coating per unit surface area will be greater on the microneedles than on the substrate. More preferably, the dried coating material is preferentially deposited on or near the tips of the microneedles. In some cases more than half, sometimes more than 90%, and occasionally more than 95% of the dried coating material by weight is deposited on the microneedles. In some cases the dried coating preferentially resides on the upper half of the microneedles, that is, the portion of the microneedles away from the substrate. In one embodiment substantially no dried coating material is deposited on the substrate, that is, substantially all of the dried coating material is deposited on the microneedles. In one embodiment, substantially all of the dried coating material is deposited on the upper half of the microneedles. By substantially all, it should be understood that insignificant amounts of dried coating material, for example less than about 5% by weight, preferably less than about 1% by weight of the dried coating material is not deposited on the upper half of the microneedles. The thickness of the dried coating material may vary depending on the location on the microneedle array and the intended application use for the coated microneedle array. Typical dried coating thicknesses are less than 50 microns, often less than 20 microns and sometimes less than 10 microns. It may be desirable for the coating thickness to be smaller near the tip of the microneedle so as not to interfere with the ability of the microneedle to effectively pierce into the skin.

In one embodiment, different portions of the coating material may be preferentially deposited in different locations on the microneedle array. For example, where the coating material comprises a pharmaceutically effective substance (such as an antigen), it may be desirable to preferentially deposit the pharmaceutically effective substance on or near the tips of the microneedles. In some cases more than half, sometimes more than 90%, and occasionally more than 95% of the pharmaceutically effective substance by weight is deposited on the microneedles. In some cases the pharmaceutically effective substance preferentially resides on the upper half of the microneedles, that is, the portion of the microneedles away from the substrate. In one embodiment substantially no pharmaceutically effective substance is deposited on the substrate, that is, substantially all of the pharmaceutically effective substance is deposited on the microneedles. In one embodiment, substantially all of the pharmaceutically effective substance is deposited on the upper half of the microneedles. By substantially all, it should be understood that insignificant amounts of pharmaceutically effective substance, for example less than about 5% by weight, preferably less than about 1% by weight of the pharmaceutically effective substance is not deposited on the upper half of the microneedles.

The dried coating material is a solid or semi-solid remaining after removal of the carrier fluid. It should be understood when referring to a dried coating material, however, that relatively small amounts of carrier fluid and/or masking fluid may remain in the resultant dried coating material. For example, where the carrier fluid comprises water, the resultant dried coating may typically contain between about 0.1 to 30% by weight of water, often between about 1% to 20% by weight of water, and sometimes between about 1% and 10% by weight of water.

A masking film, when employed, is desirably a liquid impermeable film and preferably a polymeric film. Examples of suitable polymeric films include polypropylene, polyethylene, or polyethylene terephthalate. The masking film may also have a surface coating such as a silicone or fluorochemical release coating, which may repel an aqueous coating fluid from the masking film and cause a coating solution to bead up on the exposed needle tips. Alternatively, the masking film may have a hydrophilic coating which may repel organic coating fluid from the masking film.

Figure 6C:
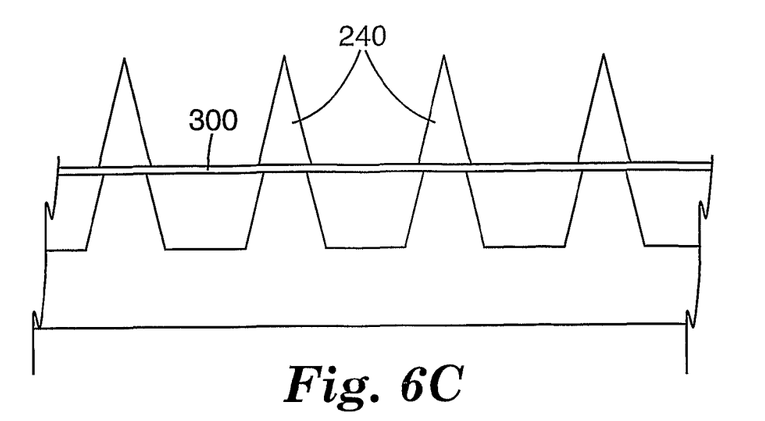
FIG. 6C is a schematic cross-sectional view of the array as the coating has evaporated to leave a dried coating.

In one aspect the masking film is removed after the carrier fluid has evaporated leaving a dry-coated microneedle array such as that shown in FIG. 3E. Alternatively, the masking film may be left in place and the dry-coated microneedle array with masking film as shown in FIG. 6C can be directly applied to a skin surface. In another alternative (not shown), the film could be pushed downwards and into contact with the substrate after the carrier fluid has evaporated. The coated array with masking film may have further utility as described in U.S. Patent Application Publication 2003/0135161, the disclosure of which is hereby incorporated by reference. The masking film may be pierced by the microneedle array by any suitable method, including a simultaneous delivery of force and ultrasonic energy and other methods described in U.S. Patent Application Publication 2003/0135161.

In one embodiment, two immiscible solutions may be agitated or stirred to form a temporarily homogeneous emulsion which can be applied to the microneedle array. After application to the microneedle array, the emulsion may then phase separate leaving a fluid layer against the substrate that serves as the masking layer and a fluid layer above which serves as the coating solution. These layers may then undergo evaporation to leave a dried coating film as described above.

In another embodiment the masking layer may be a semi-solid or solid layer that may be transformed into a liquid and subsequently removed. Examples of suitable masking layers include thermo-responsive gels, electrorheological fluids, reversible gels, such as a silica or polymeric gels that are sensitive to either pH or ions, or any other suitable transient or reversible gel.

An exemplary thermoresponsive gel that may be useful as the masking layer is a gel formed of a propylene oxide-ethylene oxide block copolymer, such as Pluronic® F-77 (available from BASF). An aqueous gel of about 1% solids may be prepared on the microneedle array by applying a solution of the thermoresponsive propylene oxide-ethylene oxide block copolymer to the substrate and then heating the array to a temperature of 34° C. or higher to form a gel. The coating solution may be applied to the exposed microneedles and subsequently dried. The dry-coated array can then be cooled back to room temperature thereby returning the gel to a liquid state which may be poured off of the array. Other examples of thermoresponsive gels may be found in U.S. Pat. No. 4,474,751, the disclosure of which is herein incorporated by reference.

A low solids content hydrogel solution that gels when exposed to salts, such as those described in U.S. Pat. Nos. 5,340,572 and 5,192,535, the disclosures of which are herein incorporated by reference, may be applied to the microneedle array substrate to provide a masking layer. A salt solution may then be added to the hydrogel solution so that the hydrogel solution gels. The coating solution may then be applied to the gelled masking layer and allowed to dry thereby leaving a dry-coated microneedle array on the exposed portions of the microneedles. The pH or ionic content of the gelled masking layer may then be altered to return the gel to a liquid state that can be easily removed from the microneedle array.

A charged colloidal fluid may be applied as the masking layer. Upon application of an electric field the colloidal fluid may form a gel that can serve as a semi-solid masking layer. The coating solution may then be applied to the gelled masking layer and allowed to dry thereby leaving a dry-coated microneedle array on the exposed portions of the microneedles. The electric field can then be removed transforming the masking layer to a liquid state and the liquid may be poured off of the array and/or evaporated.

In another embodiment, the masking layer may be a solid layer comprising a frozen fluid, such as ice. A coating solution may be applied and allowed to dry leaving a dry-coated microneedle array on the exposed portions of the microneedles. The layer of ice may then be allowed to warm and become liquid water which may be removed by any convenient means.

In any of the foregoing embodiments, any number of conventional coating methods may be used to apply the masking fluid to the array substrate or to apply a coating solution to the masked microneedle array including dipping, brushing, drop coating, precision volumetric dispensing, gravure coating, and spray coating. In one embodiment, the coating solution and/or masking solution may be applied as a metered amount of one or more droplets that are allowed to spread across the array substrate.

Figure 7:
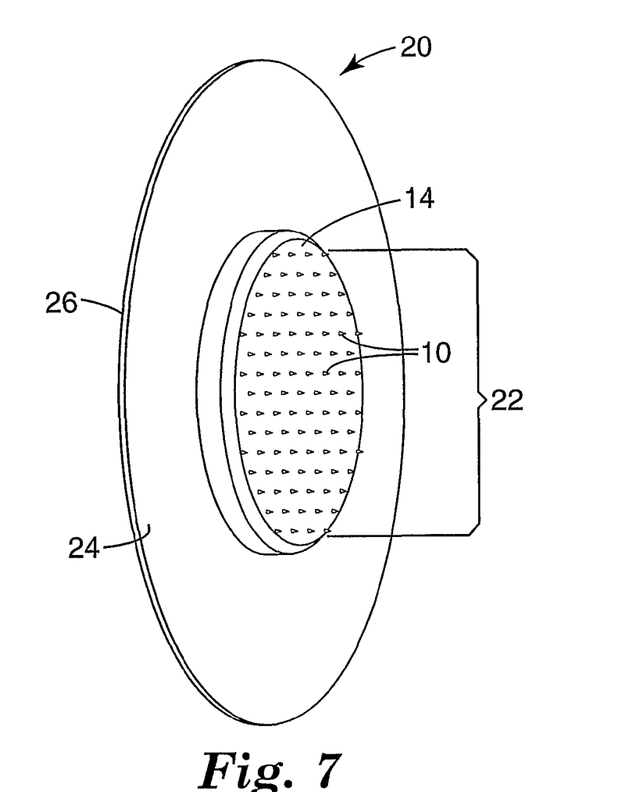
FIG. 7 is a schematic perspective view of patch microneedle device.

In one embodiment, the microneedle array shown in FIG. 3E may be applied to a skin surface in the form of a patch shown in more detail in FIG. 7. FIG. 7 illustrates a microneedle device comprising a patch 20 in the form of a combination of an array 22, pressure sensitive adhesive 24 and backing 26. A portion of the array 22 is illustrated with microneedles 10 protruding from a microneedle substrate surface 14. The microneedles 10 may be arranged in any desired pattern or distributed over the microneedle substrate surface 14 randomly. As shown, the microneedles 10 are arranged in uniformly spaced rows. In one embodiment, arrays of the present invention have a distal-facing surface area of more than about 0.1 cm$^2$ and less than about 20 cm$^2$, preferably more than about 0.5 cm$^2$ and less than about 5 cm$^2$. In one embodiment (not shown), a portion of the substrate surface 14 of the patch 20 is non-patterned. In one embodiment the non-patterned surface has an area of more than about 1 percent and less than about 75 percent of the total area of the device surface that faces a skin surface of a patient. In one embodiment the non-patterned surface has an area of more than about 0.10 square inch (0.65 cm$^2$) to less than about 1 square inch (6.5 cm$^2$). In another embodiment (shown in FIG. 7), the microneedles are disposed over substantially the entire surface area of the array 22.

The microneedle devices useful in the various embodiments of the invention may comprise any of a variety of configurations, such as those described in the following patents and patent applications, the disclosures of which are herein incorporated by reference. One embodiment for the microneedle devices comprises the structures disclosed in U.S. Patent Application Publication No. 2003/0045837. The disclosed microstructures in the aforementioned patent application are in the form of microneedles having tapered structures that include at least one channel formed in the outside surface of each microneedle. The microneedles may have bases that are elongated in one direction. The channels in microneedles with elongated bases may extend from one of the ends of the elongated bases towards the tips of the microneedles. The channels formed along the sides of the microneedles may optionally be terminated short of the tips of the microneedles. The microneedle arrays may also include conduit structures formed on the surface of the substrate on which the microneedle array is located. The channels in the microneedles may be in fluid communication with the conduit structures. Another embodiment for the microneedle devices comprises the structures disclosed in co-pending U.S. patent application Ser. No. 10/621,620 filed on Jul. 17, 2003 which describes microneedles having a truncated tapered shape and a controlled aspect ratio. Still another embodiment for the microneedle devices comprises the structures disclosed in U.S. Pat. No. 6,091,975 (Daddona, et al.) which describes blade-like microprotrusions for piercing the skin. Still another embodiment for the microneedle devices comprises the structures disclosed in U.S. Pat. No. 6,313,612 (Sherman, et al.) which describes tapered structures having a hollow central channel. Still another embodiment for the micro arrays comprises the structures disclosed in International Publication No. WO 00/74766 (Gartstein, et al.) which describes hollow microneedles having at least one longitudinal blade at the top surface of tip of the microneedle.

One or more surfaces of the microneedle arrays may be altered with a coating or surface pre-treatment prior to application of the masking layer and coating material. For example, a thin layer of material may be applied to the entire surface of the array prior to application of the masking layer. Such a coating may alter the hydrophilicity or hydrophobicity of the array and thereby affect the ability of the masking layer and/or coating solution to wet the array. Such a coating may also be partially or totally miscible with the coating solution, so that the coating is partially or totally taken up into the coating solution before the carrier solvent completely evaporates, thereby leaving a dried mixture of the coating pretreatment material and the coating material subsequently applied. Examples of such coatings include polymer coatings, dried powders, and amorphous glasses.

Examples of suitable polymer coatings include polyvinylpyrrolidone, polyvinyl alcohol, polyethylene glycol, fluoropolymers, and mixtures thereof. Such a polymer coating may be prepared on the array by applying a polymer solution (e.g., an aqueous or ethanolic solution) to the array and allowing the solvent to evaporate, thereby leaving a dried polymer coating behind. Alternatively, the coating may be directly applied as a solid material, such as through use of heat or plasma deposition. Examples of dried powders include aluminum potassium sulfate dodecahydrate, aluminum hydroxide monohydrate, sucrose, trehalose, and lactose. Examples of thin layers of material cured onto the array include plasma deposited diamond-like glass films, such as those described in U.S. Pat. No. 6,881,538 (Haddad, et al.), ultraviolet polymerized acrylates, such as those described in U.S. Pat. No. 5,440,446 (Shaw, et al.), plasma deposited fluoropolymers, or any other thin layer that may be applied by conventional coating method, such as spray coating or roll coating and subsequently crosslinked using any suitable radiation.

The surface of the microneedles may also be altered with a surface pre-treatment which simply alters the chemical functionality of the surface. Typical surface pre-treatments include a variety of plasma treatments capable of altering surface functionality. For example, polycarbonate may be plasma treated with a nitrogen plasma to cause amide functionalization or with an oxygen plasma to cause carboxylate functionalization. A combination of nitrogen and oxygen plasma treatment may be used to give a mixed surface functionality.

The coating solution may comprise one or more of a biologically active material, a pharmaceutically effective substance, and a therapeutically active substance. In one embodiment, microneedle devices suitable for use in the present invention may be used to deliver drugs (including any pharmacological agent or agents) through the skin in a variation on transdermal delivery, or to the skin for intradermal or topical treatment, such as vaccination. In one aspect, drugs that are of a large molecular weight may be delivered transdermally. Increasing molecular weight of a drug typically causes a decrease in unassisted transdermal delivery. Microneedle devices suitable for use in the present invention have utility for the delivery of large molecules that are ordinarily difficult to deliver by passive transdermal delivery. Examples of such large molecules include proteins, peptides, nucleotide sequences, monoclonal antibodies, DNA vaccines, polysaccharides, such as heparin, and antibiotics, such as ceftriaxone.

In another aspect, microneedle devices suitable for use in the present invention may have utility for enhancing or allowing transdermal delivery of small molecules that are otherwise difficult or impossible to deliver by passive transdermal delivery. Examples of such molecules include salt forms; ionic molecules, such as bisphosphonates, including sodium alendronate or pamedronate; and molecules with physicochemical properties that are not conducive to passive transdermal delivery.

In another aspect, microneedle devices suitable for use in the present invention may have utility for enhancing delivery of molecules to the skin, such as in dermatological treatments, vaccine delivery, or in enhancing immune response of vaccine adjuvants. Examples of suitable vaccines include flu vaccine, Lyme disease vaccine, rabies vaccine, measles vaccine, mumps vaccine, chicken pox vaccine, small pox vaccine, hepatitis vaccine, pertussis vaccine, rubella vaccine, diphtheria vaccine, encephalitis vaccine, yellow fever vaccine, recombinant protein vaccine, DNA vaccine, polio vaccine, therapeutic cancer vaccine, herpes vaccine, pneumococcal vaccine, meningitis vaccine, whooping cough vaccine, tetanus vaccine, typhoid fever vaccine, cholera vaccine, tuberculosis vaccine, and combinations thereof. The term "vaccine" thus includes, without limitation, antigens in the forms of proteins, polysaccharides, oligosaccharides, or weakened or killed viruses. Additional examples of suitable vaccines and vaccine adjuvants are described in U.S. Patent Application Publication No. 2004/0049150, the disclosure of which is hereby incorporated by reference.

Microneedle devices may be used for immediate delivery, that is where they are applied and immediately removed from the application site, or they may be left in place for an extended time, which may range from a few minutes to as long as 1 week. In one aspect, an extended time of delivery may from 1 to 30 minutes to allow for more complete delivery of a drug than can be obtained upon application and immediate removal. In another aspect, an extended time of delivery may be from 4 hours to 1 week to provide for a sustained release of drug.

EXAMPLES

Tetanus Toxoid Total-Array Content by High Performance Liquid Chromatography (HPLC)

A sample extraction solvent was prepared containing 50 mM potassium perchlorate, 50 mM potassium citrate, 20 mM sodium phosphate, 376 mM sodium chloride, and 100 µg/mL bovine serum albumin. An HPLC sample solution was prepared by placing an array into a polypropylene cup, adding 1.0 mL of the sample extraction solvent to the cup, snapping a cap onto the sample cup, and sonicating for 30 minutes.

Gradient elution HPLC (Mobile phase A): 0.2% (v/v) perchloric acid; Mobile phase B: 10% water, 88% acetonitrile, 2% isopropanol, 0.2% perchloric acid (70%); Solvent Program: 0.00 min, 22% B, 1.0 mL/min; 6.00 min, 58% B, 1.0 mL/min; 6.01 min, 100% B, 1.0 mL/min; 6.50 min, 100% B, 0.5 mL/min; 10.0 min, 0% B, 0.5 mL/min; Injection Volume: 100 µL; Column: Zorbax 300SB-C8 50×4.6 mm, 3.5 micron) was used to quantify tetanus toxoid in the HPLC sample solution.

Non-adjuvanted tetanus toxoid (TT) vaccine (Aventis) was calibrated against a lyophilized TT primary standard (List Biologics) and used as a working standard. The working standard was used to obtain a calibration curve from approximately 1 ug-TT/mL to 28 ug-TT/mL. The correlation coefficient for the linear regression of the calibration curve was typically greater than 0.999. Tetanus toxoid content results are the average of between 6 and 10 replicates.

Tetanus Toxoid Tip-Content by High Performance Liquid Chromatography (HPLC)

Tetanus toxoid content on the tips of the microneedles was measured by fixing the toxoid in place on the substrate and lower portions of the microneedles so that it could not be extracted into the HPLC sample solution. A microneedle array was placed on a flat surface with the needles pointing upward and 10 µL of an oil-based polyurethane coating solution (Minwax® Fast-Drying Polyurethane) was applied to the array and allowed to coat the substrate of the array. The polyurethane was allowed to cure for at least 3 hours at ambient conditions. The array was subsequently extracted and analyzed as described in the total content method.

Aluminum Content by Inductively Coupled Plasma (ICP)

A 0.5 mL aliquot of the HPLC sample solution (described above) was diluted to 5.0 mL with 4% nitric acid for analysis of aluminum by ICP. The analysis was calibrated by using aluminum standards at 1, 2, 4, 5, 6, 8 and 11 µg/mL. The correlation coefficient for the linear regression of the calibration curve was typically greater than 0.999.

Enzyme-Linked Immunosorbant Assay (ELISA)

Quantitative determination of anti-tetanus toxoid IgG from rabbit serum was performed by ELISA. Tetanus toxoid is coated on the solid phase and binds anti-tetanus toxoid IgG from rabbit serum samples. Plates are washed and bound rabbit IgG is detected with an anti-rabbit IgG-HRP conjugate. The assay was standardized against the EP veterinary standard rabbit anti-tetanus toxoid BRP Batch 1 (EDQM-European Pharmacopeia Commission catalog number C2425600). 1000 arbitrary units (AU) from this ELISA is equivalent to 1 international unit (IU). Unless otherwise noted, anti-tetanus toxoid IgG results are reported as the geometric average of 5 replicates.

Microneedle Arrays

Microneedle arrays were prepared as follows. A circular disk (area 2 cm$^2$, thickness 1.02 mm) that was partially patterned with an array of microneedles (37×37) in a square shape (1 cm$^2$) centered on one side of the disk was prepared. The needles were regularly spaced with a distance of 275 microns between the tips of adjacent needles in a square-shaped pattern. Individual needles were pyramidal in shape with a height of 250 microns and a square base having a side-length of 83.3 microns. The tips were truncated with a flat, square-shaped top having a side-length of 5 microns. Arrays were injection molded according to the general description provided in International Patent Application Publication No. WO 05/82596 and made from polycarbonate (Lexan® HPS1R-1125, GE Plastics, Pittsfield, Mass.). The center of the disk was then die cut to provide a microneedle array (area=1 cm$^2$) having microneedles on approximately 90% of the surface of the patterned side of the disk. The microneedle array had approximately 1200 microneedles.

Example 1

An aluminum mixture of 6.0 g aluminum potassium sulfate dodecahydrate (Penta, USP grade), 0.24 g aluminum hydroxide monohydrate, and 100 mL water was prepared and sonicated until the solution was nearly clear. The aluminum mixture was then spray coated for 1 minute onto an array using a Six-Jet atomizer (Model 9306, TSI Inc., Shoreview, Minn.) that was modified with a small volume reservoir, a turbulent flow generator, and an array holder. The rate of coating was nominally 20 μg of aluminum per minute. The microneedle array was then placed on a flat surface with the needles pointing upward. HFE-7500 3M™ NOVEC™ Engineered Fluid, 3-ethoxy-1,1,1,2,3,4,4,5,5,6,6,6-dodecafluoro-2-trifluoromethyl-hexane, (3M Co., St. Paul, Minn.) was used as a masking fluid. An aliquot (25 μL) of masking fluid was applied to the center of the array using a pipette and allowed to spread across the array. An antigen coating formulation was prepared by mixing equal parts of tetanus toxoid (Statens Serum Institute Lot 92-1, 888 Lf/mL) and ethanol. A 10 μL aliquot of the antigen coating formulation was applied to the center of the masking fluid on the array using a pipette. The nominal amount of tetanus toxoid in the applied antigen coating formulation was 16 μg. The antigen coating formulation and masking fluid were allowed to dry at ambient conditions for approximately 30 minutes to provide a dried antigen coating on the array. Examination of the antigen coated array by scanning electron microscopy (SEM) showed a relatively smooth coating over the microneedle surfaces. Tetanus toxoid total-array content as measured by reversed phase HPLC was 18.2 μg (st. dev.=1.2 μg). Aluminum content of the coated array as measured by ICP was 40 μg (st. dev.=10 μg).

Example 2

A coated array was prepared according to the procedure described in Example 1, with the exception that the aluminum mixture was spray coated for 3 minutes onto an array prior to application of the antigen coating formulation and a 13 μL aliquot of masking fluid was used. Examination of the antigen coated array by scanning electron microscopy (SEM) showed clumps or balls of material at or near the tips of the microneedles. Tetanus toxoid total-array content as measured by reversed phase HPLC was 19.1 μg (st. dev.=1.0 μg). Aluminum content of the coated array as measured by ICP was 57 μg (st. dev.=21 μg).

Example 3

A coated array was prepared according to the procedure described in Example 1, with the following exceptions. The antigen coating formulation was prepared by mixing one part tetanus toxoid, 3 parts water, and 4 parts ethanol. A 13 μL aliquot of masking fluid was used. The nominal amount of tetanus toxoid in the applied antigen coating formulation was 4 μg. Examination of the antigen coated array by scanning electron microscopy (SEM) showed a relatively smooth coating over the microneedle surfaces.

Tetanus toxoid total-array content as measured by reversed phase HPLC was 4.4 μg (st. dev.=0.2 μg). Aluminum content of the coated array as measured by ICP was 13 μg (st. dev.=6 μg).

Example 4

A coated array was prepared according to the procedure described in Example 3, with the exception that the aluminum mixture was spray coated for 5 minutes onto an array prior to application of the antigen coating formulation. Examination of the antigen coated array by scanning electron microscopy (SEM) showed clumps or balls of material at or near the tips of the microneedles. Tetanus toxoid total-array content array as measured by reversed phase HPLC was 4.7 μg (st. dev.=0.4 μg). Aluminum content of the coated array as measured by ICP was 94 μg (st. dev.=19 μg).

Example 5

A coated array was prepared according to the procedure described in Example 2, with the exception that the aluminum mixture was spray coated for 5 minutes onto an array prior to application of the antigen coating formulation. Examination of the antigen coated array by scanning electron microscopy (SEM) showed a relatively smooth coating over the microneedle surfaces. Tetanus toxoid total-array content as measured by reversed phase HPLC was 17.9 µg (st. dev.=0.8 µg). Aluminum content of the coated array as measured by ICP was 65 µg (st. dev.=8 µg).

Example 6

A coated array was prepared according to the procedure described in Example 1, with the following exceptions. The aluminum mixture was spray coated for 3 minutes onto an array prior to application of the antigen coating formulation. The antigen coating formulation was prepared by mixing 2 parts tetanus toxoid, 2 parts water, and 4 parts ethanol. The nominal amount of tetanus toxoid in the applied antigen coating formulation was 8 µg. Examination of the antigen coated array by scanning electron microscopy (SEM) showed a relatively smooth coating over the microneedle surfaces. Tetanus toxoid total-array content as measured by reversed phase HPLC was 7.6 µg (st. dev.=0.7 µg). Aluminum content of the coated array as measured by ICP was 23 µg (st. dev.=6 µg).

Example 7

A coated array was prepared according to the procedure described in Example 1, with the following exceptions. The aluminum mixture was prepared with a ratio of 6.0 g aluminum potassium sulfate dodecahydrate (Penta, USP grade), 0.06 g aluminum hydroxide monohydrate, and 100 mL water. The antigen coating formulation was prepared by mixing one part tetanus toxoid with one part water. A 13 µL aliquot of masking fluid was used. Ethanol (13 µL) was applied to the center of the masking fluid on the array using a pipette prior to application of the antigen coating formulation. The antigen coating formulation was then applied onto the ethanol. The nominal amount of tetanus toxoid in the applied antigen coating formulation was 16 µg. Examination of the antigen coated array by scanning electron microscopy (SEM) showed a smooth coating over the microneedle surfaces. Tetanus toxoid total-array content as measured by reversed phase HPLC was 16.8 µg (st. dev.=0.8 µg). Aluminum content of the coated array as measured by ICP was 15 µg (st. dev.=3 µg).

In Vivo Anti-Tetanus Toxoid IgG and Tetanus Toxoid Removal

Microneedle devices were prepared by adhering antigen coated arrays as described in Examples 1 to 7 to an adhesive backing. The arrays were applied to New Zealand White female rabbits (N=5) using an applicator as generally described in U.S. patent application Ser. No. 60/578,651, the disclosure of which is hereby incorporated by reference. The applicator piston mass was 2.88 g and the devices were applied at a velocity of 6.19 meters/second. An area on the abdomen of each rabbit was closely clipped and shaved, taking care not to irritate the skin. One device was applied to each rabbit and allowed to remain in place for 20 minutes before removal. A second device (with the same coating as the first device) was applied to each rabbit 14 days after the initial application and again allowed to remain in place for 20 minutes before removal. A serum sample was taken from each rabbit 21 days after the initial application and analyzed for the level of anti-tetanus toxoid IgG by ELISA. The results are summarized in Table 1. The residual amount of tetanus toxoid in the arrays removed from the rabbits was tested by HPLC. The amount of tetanus toxoid removed from the array was determined by taking the difference between the initial tetanus toxoid level and the residual tetanus toxoid level. The results are summarized in Table 2.

TABLE 1

| Array Example No. | anti-tetanus toxoid IgG [AU] | tetanus toxoid removed [µg] |
|---|---|---|
| 1 | 3981 | 2.4 |
| 2 | 1536 | 2.8 |
| 3 | 3771 | 0.5 |
| 4 | 437 | 0.5 |
| 5 | 2866 | 3.0 |
| 6 | 3679 | 1.0 |
| 7 | 2957 | 3.6 |

Example 8

A coated array was prepared according to the procedure described in Example 1, with the exception that the masking fluid used was FC-43 FLUORINERT™ Electronic Liquid, a mixture of primarily 12 carbon perfluoro compounds, (3M Co., St. Paul, Minn.) and the amount of masking fluid applied was 15 µL. Tetanus toxoid content of the coated array as measured by reversed phase HPLC was 17.6 µg (st. dev.=1.8 µg). Tetanus toxoid content on the tips of the microneedles was measured as 2.7 µg (st. dev.=0.2 µg).

Example 9

A microneedle array was placed on a flat surface with the needles pointing upward. FC-43 FLUORINERT™ Electronic Liquid was used as a masking fluid. An aliquot (15 µL) of masking fluid was applied to the center of the array using a pipette and allowed to spread across the array. An antigen coating formulation was prepared by mixing equal parts of tetanus toxoid (Statens Serum Institute Lot 92-1, 888 Lf/mL) and ethanol. A 10 µL aliquot of the antigen coating formulation was applied to the center of the masking fluid on the array using a pipette. The nominal amount of tetanus toxoid in the applied antigen coating formulation was 16 µg. The antigen coating formulation and masking fluid were allowed to dry at ambient conditions for approximately 30 minutes to provide a dried antigen coating on the array. Tetanus toxoid total-array content as measured by reversed phase HPLC was 23.6 µg (st. dev.=0.1 µg). Tetanus toxoid tip-content was measured as 21.7 µg (st. dev.=1.2 µg).

Example 10

A polyvinylpyrrolidone (PVP) stock solution was prepared by adding 825 mg PVP (Plasdone® K-29/32, Povidone USP, ISP Technologies, Wayne, N.J.) to 25 mL water and mixing until the PVP was dissolved. A stock solution was prepared by adding 50 mg polysorbate 80 (Tween®-80, Sigma Chemical Co., St. Louis, Mo.) to 25 mL ethanol. A diluted stock solution was prepared by adding 2 mL of the polysorbate stock solution to 18 mL ethanol. A PVP priming solution was prepared by adding 1 mL of the PVP stock solution to 9 mL of the diluted polysorbate stock solution. A microneedle array was placed on a flat surface with the needles pointing upward and an aliquot of 30 µL of the PVP priming solution was applied to the center of the array using a pipette and allowed to spread across the array. The PVP priming solution was allowed to dry at ambient conditions.

Tween®-80 (90 mg) was added to water (30 mL) to prepare a Tween®-80 stock solution with a concentration of 3 mg/mL. PVP (1.8 g) was added to water (20 mL) to prepare a PVP stock solution with a concentration of 90 mg/mL. Sucrose (1.8 g) was added to water (20 mL) to prepare a sucrose stock solution with a concentration of 90 mg/mL. Potassium citrate (1.8 g) was added to water (20 mL) to prepare a potassium citrate stock solution with a concentration of 90 mg/mL. An antigen coating formulation was prepared by mixing tetanus toxoid (Statens Serum Institute Lot 92-1, 888 Lf/mL) with aliquots of the Tween®-80, PVP, sucrose and potassium citrate stock solutions.

An aliquot (15 μL) of masking fluid (FC-43 FLUORINERT™ Electronic Liquid) was applied to the center of the array using a pipette and allowed to spread across the array. A 10 μL aliquot of the antigen coating formulation was applied to the center of the masking fluid on the array using a pipette. The nominal amount of tetanus toxoid in the applied antigen coating formulation was 10 μg. The nominal amount of Tween®-80 in the applied antigen coating formulation was 6 μg. The nominal amounts of PVP, sucrose, and potassium citrate were 100 μg. The antigen coating formulation and masking fluid were allowed to dry at ambient conditions for approximately 30 minutes to provide a dried antigen coating on the array. Tetanus toxoid total-array content as measured by reversed phase HPLC was 11.9 μg (st. dev.=0.5 μg). Tetanus toxoid tip-content was measured as 5.0 μg (st. dev.=1.2 μg).

Examples 11-14

Coated arrays were prepared according to the procedure described in Example 10 with the exception that the nominal amounts of PVP, sucrose and potassium citrate were varied, as shown in Table 2. Tetanus toxoid content of the coated array as measured by reversed phase HPLC and tetanus toxoid content on the tips of the microneedles was measured. The results are shown in Table 2.

TABLE 2

| Ex. No. | PVP [μg] | Sucrose [μg] | Potassium citrate [μg] | Tetanus toxoid content: Total-array, Mean (st. dev) [μg] | Tetanus toxoid content: Tip-content, Mean (st. dev) [μg] |
|---|---|---|---|---|---|
| 10 | 100 | 100 | 100 | 11.9 (0.5) | 5.0 (1.2) |
| 11 | 100 | 100 | 10 | 13.1 (0.4) | 8.5 (0.5) |
| 12 | 10 | 10 | 100 | 11.6 (0.8) | 9.3 (1.3) |
| 13 | 10 | 100 | 10 | 11.5 (0.3) | 9.1 (1.4) |
| 14 | 100 | 10 | 10 | 12.3 (0.3) | 6.9 (0.7) |

In Vivo Tetanus Toxoid Deposition

Microneedle devices were prepared by adhering antigen coated arrays as described in Examples 10 to 14 to an adhesive backing. The arrays were applied to hairless guinea pigs using an applicator as generally described in U.S. patent application Ser. No. 60/578, 651, the disclosure of which is hereby incorporated by reference. The applicator piston mass was 5.08 g and the devices were applied at a velocity of 8.07 meters/second. The devices were applied to sites on the soft tissue of the abdomen and muscle on the lower back below the ribs and just above the pelvis. The application sites were cleaned with 70% isopropyl alcohol and allowed to air dry for at least 30 seconds prior to device application. Devices (N=5) were removed at specified time points and the tetanus toxoid content remaining on the arrays was measured by HPLC. The results are summarized in Table 3.

TABLE 3

| Array Example No. | tetanus toxoid content [μg]: T = 0 min | T = 1 min | T = 5 min | T = 10 min | T = 20 min |
|---|---|---|---|---|---|
| 10 | 11.9 | 9.8 | 10.3 | 8.6 | 8.1 |
| 11 | 13.1 | 10.9 | 10.1 | 8.2 | 8.1 |
| 12 | 11.6 | 9.1 | 8.1 | 7.6 | 6.3 |
| 13 | 11.5 | 9.9 | 8.6 | 8.2 | 7.0 |
| 14 | 12.3 | 11.1 | 9.8 | 10.0 | 8.5 |

Example 15

A polyvinyl alcohol priming solution was prepared as follows. An amount (250 mg) of polyvinyl alcohol (80% hydrolyzed, typical Mw=9,000-10,000, CAS 9002-89-5, Aldrich, St. Louis, Mo.) was added to water (25 mL) to prepare a polyvinyl alcohol stock solution. An aliquot of polyvinyl alcohol stock solution (2 mL) was added to ethanol (18 mL) to prepare a polyvinyl alcohol priming solution. A microneedle array was placed on a flat surface with the needles pointing upward and an aliquot of 30 μL of the polyvinyl alcohol priming solution was applied to the center of the array using a pipette and allowed to spread across the array. The polyvinyl alcohol priming solution was allowed to dry at ambient conditions. An aliquot (15 μL) of masking fluid (FC-43 FLUORINERT™ Electronic Liquid) was then applied to the center of the array using a pipette and allowed to spread across the array. A 10 μL aliquot of the antigen coating formulation was applied to the center of the masking fluid on the array using a pipette. Antigen coating formulations were prepared according to the general procedure described in Example 10. The nominal amount of tetanus toxoid in the applied antigen coating formulation was 10 μg. The nominal amount of Tween®-80 in the applied antigen coating formulation was 6 μg. The nominal amounts of PVP, sucrose, and potassium citrate were 100 μg. The antigen coating formulation and masking fluid were allowed to dry at ambient conditions for approximately 30 minutes to provide a dried antigen coating on the array. Tetanus toxoid total-array content as measured by reversed phase HPLC was 10.4 μg (st. dev.=0.7 μg). Tetanus toxoid tip-content was measured as 9.3 μg (st. dev.=0.4 μg).

Examples 16-23

Coated arrays were prepared according to the procedure described in Example 15 with the exception that the nominal amounts of PVP, sucrose and potassium citrate were varied, as shown in Table 4. Tetanus toxoid content of the coated array as measured by reversed phase HPLC and tetanus toxoid content on the tips of the microneedles was measured. The results are shown in Table 4.

TABLE 4

| Ex. No. | PVP [μg] | Sucrose [μg] | Potassium citrate [μg] | Tetanus toxoid content: Total-array, Mean (st. dev) [μg] | Tetanus toxoid content: Tip-content, Mean (st. dev) [μg] |
|---|---|---|---|---|---|
| 15 | 100 | 100 | 100 | 10.4 (0.7) | 9.3 (0.4) |
| 16 | 100 | 100 | 10 | 10.4 (0.3) | 8.2 (0.8) |
| 17 | 100 | 10 | 100 | 10.2 (0.6) | 9.1 (0.3) |
| 18 | 10 | 100 | 100 | 9.5 (0.9) | 6.7 (1.0) |

TABLE 4-continued

| Ex. No. | PVP [µg] | Sucrose [µg] | Potassium citrate [µg] | Total-array, Mean (st. dev) [µg] | Tip-content, Mean (st. dev) [µg] |
|---|---|---|---|---|---|
| 19 | 10 | 10 | 100 | 9.3 (0.4) | 5.8 (1.1) |
| 20 | 10 | 100 | 10 | 9.5 (0.5) | 6.9 (0.9) |
| 21 | 100 | 10 | 10 | 10.2 (0.4) | 5.6 (1.4) |
| 22 | 10 | 10 | 10 | 7.9 (0.2) | 4.5 (0.7) |
| 23 | 55 | 55 | 55 | 10.6 (0.4) | 8.4 (0.5) |

Example 24

A coated array was prepared according to the procedure described in Example 16. Tetanus toxoid total-array content as measured by reversed phase HPLC was 10.7 µg (st. dev.=0.9 µg). Tetanus toxoid tip-content was measured as 8.7 µg (st. dev.=0.6 µg). Arrays were applied to hairless guinea pigs as described above in the section "in vivo tetanus toxoid deposition". The amount of tetanus toxoid remaining on the array after removal from the hairless guinea pig was measured by HPLC. The results are summarized in Table 5.

Example 25

A coated array was prepared according to the procedure described in Example 17. Tetanus toxoid total-array content as measured by reversed phase HPLC was 11.4 µg (st. dev.=0.3 µg). Tetanus toxoid tip-content was measured as 8.6 µg (st. dev.=0.5 µg). Arrays were applied to hairless guinea pigs as described above in the section "in vivo tetanus toxoid deposition". The amount of tetanus toxoid remaining on the array after removal from the hairless guinea pig was measured by HPLC. The results are summarized in Table 5.

Example 26

A coated array was prepared according to the procedure described in Example 18. Tetanus toxoid total-array content as measured by reversed phase HPLC was 10.8 µg (st. dev.=0.3 µg). Tetanus toxoid tip-content was measured as 6.8 µg (st. dev.=0.9 µg). Arrays were applied to hairless guinea pigs as described above in the section "in vivo tetanus toxoid deposition". The amount of tetanus toxoid remaining on the array after removal from the hairless guinea pig was measured by HPLC. The results are summarized in Table 5.

Example 27

A coated array was prepared according to the procedure described in Example 22. Tetanus toxoid total-array content as measured by reversed phase HPLC was 11.7 µg (st. dev.=0.3 µg). Tetanus toxoid tip-content was measured as 5.3 µg (st. dev.=1.0 µg). Arrays were applied to hairless guinea pigs as described above in the section "in vivo tetanus toxoid deposition". The amount of tetanus toxoid remaining on the array after removal from the hairless guinea pig was measured by HPLC. The results are summarized in Table 5.

TABLE 5

| Array Example No. | tetanus toxoid content [µg]: T = 0 min | T = 1 min | T = 5 min | T = 10 min | T = 20 min |
|---|---|---|---|---|---|
| 24 | 10.7 | 10.6 | 8.8 | 7.8 | 6.3 |
| 25 | 11.4 | 10.2 | 8.4 | 8.1 | 7.3 |
| 26 | 10.8 | 9.3 | 9.2 | 8.4 | 7.5 |
| 27 | 11.7 | 9.7 | 9.7 | 8.3 | 7.9 |

Example 28

Microneedle arrays were prepared as described above and treated as follows. The arrays were plasma treated using a Plasma-Therm VII 7000 series plasma processing system. A diamond-like glass thin film was formed through plasma deposition by feeding a mixture of tetramethyl silane (150 standard cubic centimeter per minute, sccm) and oxygen (200 sccm) gas in an unpressurized plasma with 2000 W RF power applied for 15 seconds. The arrays were then subsequently treated with an oxygen plasma (400 sccm) under a pressure of 150 mTorr with 300 W power for 60 seconds to remove elemental and covalently bonded carbon from the surface atomic layers and to make the surface hydrophilic.

An aliquot (15 µL) of masking fluid (FC-43 FLUORINERT™ Electronic Liquid) was applied to the center of the array using a pipette and allowed to spread across the array. A 10 µL aliquot of the antigen coating formulation was applied to the center of the masking fluid on the array using a pipette. Antigen coating formulations were prepared according to the general procedure described in Example 10. The nominal amount of tetanus toxoid in the applied antigen coating formulation was 10 µg. The nominal amount of Tween®-80 in the applied antigen coating formulation was 6 µg. The nominal amounts of PVP, sucrose, and potassium citrate were 100 µg. The antigen coating formulation and masking fluid were allowed to dry at ambient conditions for approximately 30 minutes to provide a dried antigen coating on the array. Tetanus toxoid total-array content as measured by reversed phase HPLC was 12.1 µg (st. dev.=0.6 µg). Tetanus toxoid tip-content was measured as 9.6 µg (st. dev.=1.2 µg). Arrays were applied to hairless guinea pigs as described above in the section "in vivo tetanus toxoid deposition". The amount of tetanus toxoid remaining on the array after removal from the hairless guinea pig was measured by HPLC. The results are summarized in Table 7.

Examples 29-32

Coated arrays were prepared according to the procedure described in Example 28 with the exception that the nominal amounts of PVP, sucrose and potassium citrate were varied, as shown in Table 6. Tetanus toxoid content of the coated array as measured by reversed phase HPLC and tetanus toxoid content on the tips of the microneedles was measured. The results are shown in Table 6. Arrays were applied to hairless guinea pigs as described above in the section "in vivo tetanus toxoid deposition". The amount of tetanus toxoid remaining on the array after removal from the hairless guinea pig was measured by HPLC. The results are summarized in Table 7.

TABLE 6

| Ex. No. | PVP [μg] | Sucrose [μg] | Potassium citrate [μg] | Tetanus toxoid content | |
|---|---|---|---|---|---|
| | | | | Total-array, Mean (st. dev) [μg] | Tip-content, Mean (st. dev) [μg] |
| 28 | 100 | 100 | 100 | 12.1 (0.6) | 9.6 (1.2) |
| 29 | 100 | 100 | 10 | 12.4 (0.4) | 9.3 (1.7) |
| 30 | 10 | 10 | 100 | 12.3 (0.4) | 8.3 (0.8) |
| 31 | 10 | 100 | 10 | 11.3 (0.4) | 8.3 (1.3) |
| 32 | 100 | 10 | 10 | 12.3 (0.3) | 8.4 (2.0) |

TABLE 7

| Array Example No. | tetanus toxoid content [μg] | | | | |
|---|---|---|---|---|---|
| | T = 0 min | T = 1 min | T = 5 min | T = 10 min | T = 20 min |
| 28 | 12.1 | 9.6 | 9.7 | 8.0 | 8.4 |
| 29 | 12.4 | 10.5 | 9.8 | 8.4 | 7.9 |
| 30 | 12.3 | 10.7 | 10.4 | 10.1 | 10.2 |
| 31 | 11.3 | 8.4 | 9.1 | 8.3 | 7.6 |
| 32 | 12.3 | 10.4 | 9.5 | 7.7 | 8.2 |

Example 33

A stock solution was prepared by mixing sucrose (1.053 g) and Tween®-80 (0.1053 g) in 100 mL of water. An amount (1.0 mL) of 0.02 micron fluorescent beads (FluoSpheres carboxylate-modified microspheres, red fluorescent (580/605), 2.0% solids from Molecular Probes, Inc., Eugene, Oreg.) was added to 19 mL of the sucrose stock solution to prepare a coating formulation. The nominal concentration of sucrose was 1.0% (w/v), Tween®-80 was 0.1% (w/v), and fluorescent beads was 0.1% (w/v).

Microneedle arrays were prepared as described above and treated as follows. The arrays were plasma treated using a Plasma-Therm VII 7000 series plasma processing system. A diamond-like glass thin film was formed through plasma deposition by feeding a mixture of tetramethyl silane (150 standard cubic centimeter per minute, sccm) and oxygen (500 sccm) gas to form a plasma under a pressure of 300 mTorr with 500 W RF power applied for 2 minutes. The arrays were then subsequently treated with an oxygen plasma (500 sccm) under a pressure of 300 mTorr with 300 W power for 2 minutes to remove elemental and covalently bonded carbon from the surface atomic layers and to make the surface hydrophilic. Equivalent surface treatment of a flat polycarbonate sheet resulted in a material having an advancing contact angle of 8° with deionized water at room temperature.

The treated microneedle array was placed on a flat surface with the needles pointing upward. FC-43 FLUORINERT™ Electronic Liquid was used as a masking fluid. An aliquot (15 μL) of masking fluid was applied to the center of the array using a pipette and allowed to spread across the array. A 10 μL aliquot of the coating formulation was applied to the center of the masking fluid on the array using a pipette and allowed to spread. The coating formulation and masking fluid were allowed to dry at ambient conditions for at least 12 hours to provide a dried coating on the array. The array was observed by visual microscopy and the percentage of microneedles covered by the dried coating was determined. Approximately 100 percent of the microneedles were covered by the dried coating.

Example 34

A microneedle array was coated as described in Example 33 with the exception that the diamond-like glass thin film was formed with a mixture of tetramethyl silane (50 sccm) and oxygen (500 sccm). Equivalent surface treatment of a flat polycarbonate sheet resulted in a material having an advancing contact angle with deionized water at room temperature. The array was observed by visual microscopy and the percentage of microneedles covered by the dried coating was determined. Approximately 24 percent of the microneedles were covered by the dried coating.

Example 35

A microneedle array was coated as described in Example 33 with the exception that the diamond-like glass thin film was formed with a mixture of tetramethyl silane (150 sccm) and oxygen (500 sccm). Equivalent surface treatment of a flat polycarbonate sheet resulted in a material having an advancing contact angle of 40° with deionized water at room temperature. The array was observed by visual microscopy and the percentage of microneedles covered by the dried coating was determined. Approximately 20 percent of the microneedles were covered by the dried coating.

Example 36

A microneedle array was coated as described in Example 33 with the exception that the coating formulation was prepared with a nominal sucrose concentration of 25% (w/v). The array was observed by visual microscopy and the percentage of microneedles covered by the dried coating was determined. Approximately 61 percent of the microneedles were covered by the dried coating.

Example 37

A microneedle array was coated as described in Example 34 with the exception that the coating formulation was prepared with a nominal sucrose concentration of 25% (w/v). The array was observed by visual microscopy and the percentage of microneedles covered by the dried coating was determined. Approximately 27 percent of the microneedles were covered by the dried coating.

Example 38

A microneedle array was coated as described in Example 35 with the exception that the coating formulation was prepared with a nominal sucrose concentration of 25% (w/v). The array was observed by visual microscopy and the percentage of microneedles covered by the dried coating was determined. Approximately 19 percent of the microneedles were covered by the dried coating.

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

We claim:

1. A method of coating a microneedle array comprising:
   providing a microneedle array having a substrate and at least one needle;
   providing a removable masking layer on the microneedle array such that the substrate is at least partially covered by the masking layer and the at least one needle remains at least partially exposed; and
   applying a coating material to at least a portion of the exposed portion of the microneedle array.

2. A method according to claim 1 wherein the masking layer is a fluid.

3. A method according to claim 2 wherein the coating material is applied from a coating solution comprising a carrier fluid and further comprising the step of evaporating the carrier fluid thereby providing a dried coating.

4. A method according to claim 3 wherein the density of the masking layer fluid is higher than the density of the carrier fluid.

5. A method according to claim 3 wherein the volatility of the masking layer fluid is lower than that of the carrier fluid.

6. A method according to claim 3 wherein the carrier fluid is substantially immiscible with the masking layer fluid.

7. A method according to claim 3 further comprising the step of allowing the masking layer fluid to evaporate.

8. A method according to claim 7 wherein the carrier fluid is allowed to completely evaporate prior to complete evaporation of the masking layer fluid.

9. A method according to claim 2 wherein the masking layer fluid is a fluorinated liquid.

10. A method according to claim 1 wherein the microneedle array comprises a plurality of needles.

11. A method according to claim 10 wherein more than 50% by weight of the coating material applied to the microneedle array is present on the needles.

12. A method according to claim 1 wherein the masking layer is a solid or a semi-solid that may be transformed into a liquid.

13. A method according to claim 12 wherein the transformation of the masking layer is caused by a change in temperature, electric field, or pH.

14. A method according to claim 3 wherein the coating solution comprises a therapeutically active substance.

15. A method according to claim 14 wherein more than 50% by weight of the therapeutically active substance applied to the microneedle array is present on the needles.

16. A method according to claim 3 wherein the coating solution comprises water.

17. A method according to claim 3 wherein the coating solution comprises a vaccine, vaccine adjuvant, or mixture thereof.

18. A method according to claim 1 wherein the coating material is preferentially deposited onto the microneedles.

19. A method according to claim 1 wherein the coating material is preferentially deposited on or near the tips of the microneedles.

20. A method according to claim 1 wherein the removable masking layer is initially applied to the microneedle array such that no microneedle is exposed and the masking layer is subsequently allowed to partially evaporate thereby providing at least one partially exposed needle.

21. A method according to claim 20 whereby the coating material is initially applied to the masking layer and application of the coating material to at least a portion of the exposed portion of the microneedle array occurs as the masking layer evaporates.

22. A method according to claim 1 wherein the coating material comprises a carrier fluid.

23. A method according to claim 3 wherein the coating solution comprises a suspension of dispersed particles.

24. A method according to claim 1 wherein at least a portion of the surface of the microneedles is plasma treated prior to the step of providing the removable masking layer on the microneedle array.

25. A method according to claim 24 wherein the plasma comprises oxygen or nitrogen.

26. A method according to claim 1 wherein a solid coating is provided on at least a portion of the surface of the microneedles prior to the step of providing the removable masking layer on the microneedle array.

27. A method according to claim 26 wherein the solid coating comprises polyvinylpyrrolidone, polyvinyl alcohol, potassium citrate, or a diamond-like glass.

28. A method according claim 1 wherein a solvent is applied to the masking layer prior to the step of applying the coating material to at least a portion of the exposed portion of the microneedle array.

* * * * *

UNITED STATES PATENT AND TRADEMARK OFFICE
CERTIFICATE OF CORRECTION

PATENT NO. : 7,846,488 B2
APPLICATION NO. : 11/718737
DATED : December 7, 2010
INVENTOR(S) : Peter R Johnson It is certified that error appears in the above-identified patent and that said Letters Patent is hereby corrected as shown below:

Column 4
Line 62, delete "heptane" and insert in place thereof --heptane.--.

Column 9
Line 59, delete "pamedronate" and insert in place thereof --pamidronate--.

Column 10
Line 10, delete "polysaccarides, oligosaccarides," and insert in place thereof --polysaccharides, oligosaccharides,--.

Column 11
Line 14, delete "Immunosorbant" and insert in place thereof --Immunosorbent--.

Column 22
Line 41, Claim 28, after "according" insert --to--.

Signed and Sealed this
Fifteenth Day of February, 2011

David J. Kappos
*Director of the United States Patent and Trademark Office*